United States Patent
Camarero Díez et al.

(10) Patent No.: US 11,666,677 B2
(45) Date of Patent: Jun. 6, 2023

(54) DEVICE FOR EVAPORATING VOLATILE SUBSTANCES

(71) Applicant: ZOBELE HOLDING S.P.A., Trento (IT)

(72) Inventors: Roberto Camarero Díez, Barcelona (ES); Cedric Gobber, Barcelona (ES); Alba Graus Ferrer, Barcelona (ES)

(73) Assignee: ZOBELE HOLDING S P A., Trento (IT)

( * ) Notice: Subject to any disclaimer, the term of this patent is extended or adjusted under 35 U.S.C. 154(b) by 235 days.

(21) Appl. No.: 16/958,197

(22) PCT Filed: Dec. 26, 2018

(86) PCT No.: PCT/EP2018/086880
§ 371 (c)(1),
(2) Date: Jun. 26, 2020

(87) PCT Pub. No.: WO2019/129785
PCT Pub. Date: Jul. 4, 2019

(65) Prior Publication Data
US 2021/0069366 A1  Mar. 11, 2021

(30) Foreign Application Priority Data
Dec. 27, 2017 (ES) ................. ES201731477

(51) Int. Cl.
*A61L 9/12* (2006.01)
*B01F 23/21* (2022.01)
(Continued)

(52) U.S. Cl.
CPC .............. *A61L 9/12* (2013.01); *A01M 1/2077* (2013.01); *A61L 9/037* (2013.01); *A61L 9/127* (2013.01); *B01F 23/21* (2022.01)

(58) Field of Classification Search
CPC ........... B01D 23/21; A61L 9/127; B01F 23/21
See application file for complete search history.

(56) References Cited

U.S. PATENT DOCUMENTS 4,714,984 A   12/1987  Spector
5,735,460 A    4/1998  Eisenbraun
(Continued)

FOREIGN PATENT DOCUMENTS

DE   36 09 511 A1   10/1986
WO   2003/013618 A1  2/2003
(Continued)

OTHER PUBLICATIONS

International Search Report received for PCT Patent Application No. PCT/EP2018/086880 dated May 7, 2019, 4 page.
(Continued)

*Primary Examiner* — Robert A Hopkins
(74) *Attorney, Agent, or Firm* — Amster, Rothstein & Ebenstein LLP

(57) ABSTRACT

The device for evaporating volatile substances comprises a casing (1) provided with a housing for the placement of a refill (2) containing the volatile substances, and is characterised in that said casing (1) comprises a surface (3) provided with at least one coupling element (5) in order to couple an additional element (4), said additional element comprising a frame (7) and a releasable sheet (8).
It provides an evaporation device that can be easily customised.

8 Claims, 2 Drawing Sheets

(51) Int. Cl.
*A01M 1/20* (2006.01)
*A61L 9/03* (2006.01)

(56) References Cited

U.S. PATENT DOCUMENTS

| | | |
|---|---|---|
| D501,545 S | 2/2005 | Wirthman et al. |
| 9,833,530 B2 * | 12/2017 | Gordon .................. A61L 9/03 |
| 2006/0000920 A1 | 1/2006 | Leonard |
| 2007/0237498 A1 | 10/2007 | Helf et al. |

FOREIGN PATENT DOCUMENTS

| | | |
|---|---|---|
| WO | 2003/070287 A1 | 8/2003 |
| WO | 2014/071030 A1 | 5/2014 |
| WO | 2016/207430 A1 | 12/2016 |

OTHER PUBLICATIONS

Written Opinion received for PCT Patent Application No. PCT/EP2018/086880, 6 page.

* cited by examiner

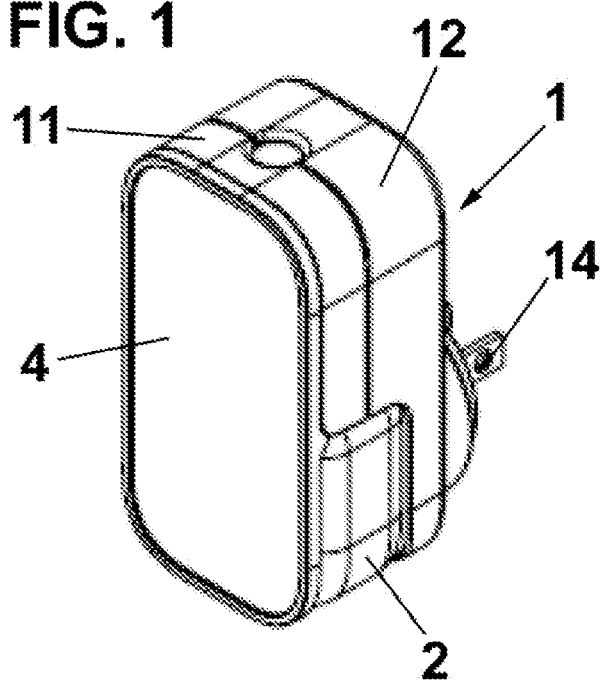
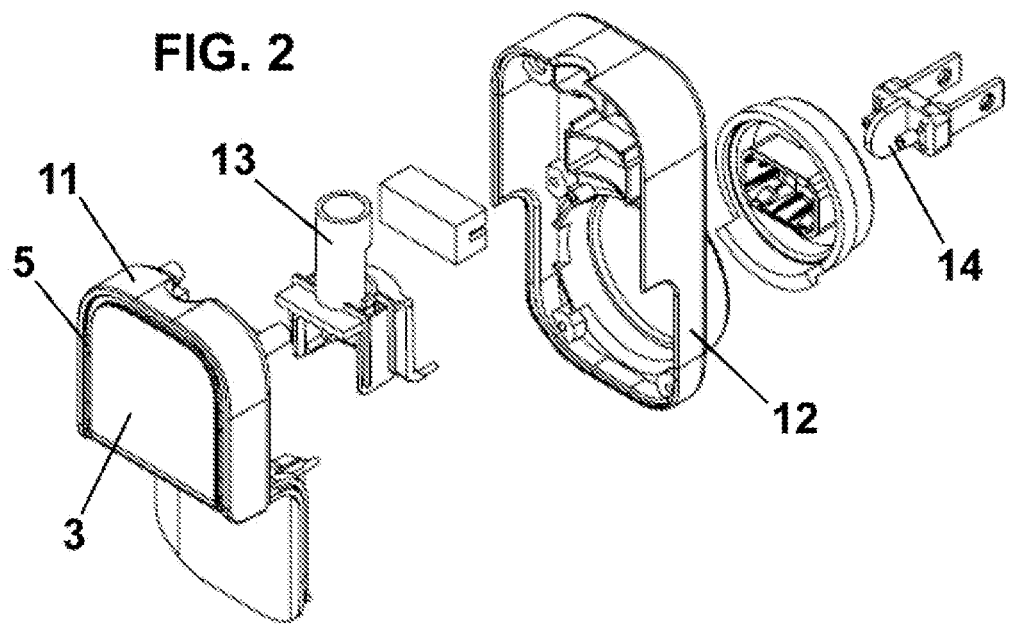

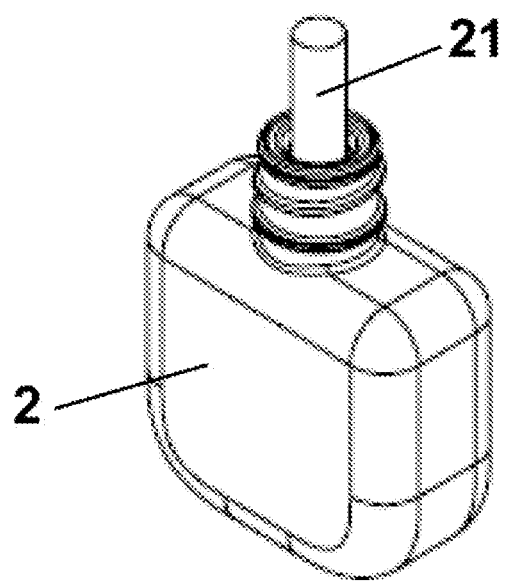
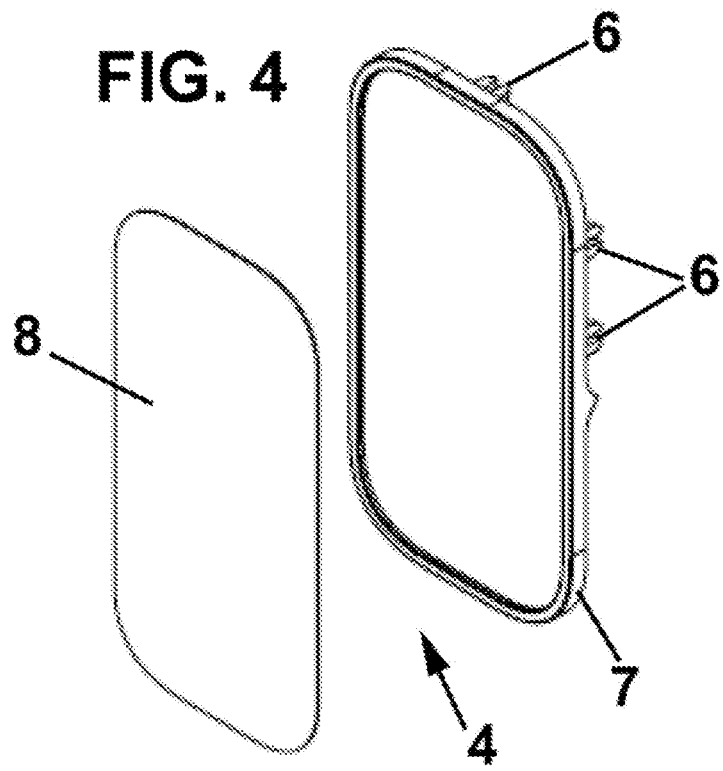

DEVICE FOR EVAPORATING VOLATILE SUBSTANCES

This application is a National Stage entry under 35 U.S.C. 371 of International Patent Application No. PCT/EP2018/086880, filed on Dec. 26, 2018, which claims priority from Spanish Patent Application No. P201731477, filed Dec. 27, 2017, the entire contents of each of which are incorporated by reference herein.

FIELD

The present invention relates to a device for evaporating volatile substances, such as an air freshener or insecticide, which enables the manufacturing thereof with a reduced cost and the customisation thereof.

BACKGROUND OF THE INVENTION

Devices for evaporating volatile substances are used as air fresheners or insecticides.

These evaporation devices comprise a casing wherein a refill containing the volatile substances to be evaporated is housed or connected. Said refill usually comprises a wick, through which the volatile substances evaporate, which is normally heated by means of an electrical resistor, which can be powered through the electrical grid by means of a plug of the casing.

Evaporation devices have many different shapes and designs, since the companies that sell them want to customise them in order to distinguish them in the market and make them more attractive to consumers. This creates a drawback for the manufacturers of these evaporation devices, since this customisation requires an additional cost, which can be significant due to the use of different shaped parts for each client which require the use of different moulds.

Therefore, an objective of the present invention is to provide a device for evaporating volatile substances, the customisation of which has the lowest cost possible, providing a casing to which a customisable element can be added.

SUMMARY OF THE INVENTION

The evaporation device of the invention resolves the aforementioned drawbacks and has other advantages which are described below.

The device for evaporating volatile substances according to the present invention comprises a casing provided with a housing for the placement of a refill containing the volatile substances, and is characterised in that said casing comprises a surface provided with at least one coupling element in order to couple an additional element, said additional element comprising a frame and a releasable sheet, said sheet being customisable.

Thanks to this characteristic, the evaporation device according to the present invention can be easily customised, adding said additional customised element or even not placing it. Thus, the manufacturing cost thereof is reduced, since the casing can be used for evaporation devices with different customised designs.

According to different alternative embodiments, said at least one coupling element can be a slot placed close to at least one portion of the outer edge of the surface, or said at least one coupling element can be a plurality of recesses and/or projections that are complementary with projections and/or recesses of said plate.

Advantageously, said casing comprises a front body and a rear body able to be coupled together, and said surface is preferably arranged in said front body.

In the device for evaporating volatile substances according to the present invention, the casing also comprises a ventilation body, through which the volatile substances evaporate, and a plug for the connection thereof to an electrical grid.

Advantageously, the area of said additional element is larger than the area of the substantially flat area of said casing, such that the area for customisation is larger. Furthermore, said additional element is preferably a plate, for example, made of plastic, although it could be made of any suitable material, which can comprise an outer frame.

Advantageously, the additional element is formed by: the frame is made of plastic and the sheet is made of a non-plastic material in the shape of a sheet, or even the additional element is formed by a plastic frame in order to protect the sheet from the evaporation of volatile substances that could degrade it.

BRIEF DESCRIPTION OF THE DRAWINGS

For the purpose of helping to make the foregoing description more readily understandable, it is accompanied by a set of drawings which, schematically and by way of illustration and not limitation, represent an embodiment.

FIG. 1 is a perspective view of a device for evaporating volatile substances according to the present invention;

FIG. 2 is an exploded view of the casing of the device for evaporating volatile substances according to the present invention;

FIG. 3 is a perspective view of the refill of the device for evaporating volatile substances according to the present invention; and FIG. 4 is a perspective view of the additional element of the device for evaporating volatile substances according to the present invention.

DESCRIPTION OF A PREFERRED EMBODIMENT

As shown in FIG. 1, the device for evaporating volatile substances according to the present invention comprises a casing 1 and a refill 2, which is what contains the volatile substances.

Said casing 1 comprises a substantially flat surface 3, which is provided with at least one coupling element for the coupling of an additional element 4, which is formed by a frame 7 and a sheet 8, said sheet 8 being mounted in a releasable manner in the frame 7, and said sheet 8 being customisable. Said surface 3 can be seen in FIG. 2.

In the embodiment shown, said at least one coupling element is a slot 5 arranged around the outer edge of a portion of said surface 3, although it could be any suitable coupling element, for example, projections and/or recesses complementary to the additional element 4.

In this embodiment, for the coupling thereof, the additional element 4 comprises a plurality of projections 6 that are housed inside said slot 5 for the pressurised coupling thereof in a releasable manner, such that it can be easily placed and removed.

It should be noted that in the evaporation device of the present invention said additional element 4 is not essential for the operation thereof, since the device also operates with the casing 1 and the refill 2, and said additional element 4 could be sold separately as an accessory. Said additional element 4 serves to customise the device thanks to the placement of the sheet 8 that is desired, and the presence of said at least one coupling element in the casing 1 enables the same casing to be used for devices with different appearances, with the customised additional element 4.

Said additional element 4 is preferably a plastic frame, and the area thereof is larger than the area defined by said surface 3, such that the area to be customised can be larger. "Customise" is understood as the possibility of the sheet 8 of the additional element 4 to have the design that is desired, or an image or texture to differentiate it from other evaporation devices.

Said sheet 8 can also be made of plastic or any suitable material. Furthermore, said sheet 8 can have any suitable thickness, depending on what is needed.

According to a preferred embodiment, shown in FIG. 2, said casing 1 is formed starting from a front body 11 and a rear body 12 coupled together, although it could be formed in any other manner. Said casing 1 also comprises a ventilation body 13 through which the volatile substances evaporate.

Said casing 1 also comprises a plug 14 for the connection thereof to the electrical grid, which enables activating an electrical resistor in order to increase the evaporation of the volatile substances.

An example of the refill 2 that is preferably used in the evaporation device according to the present invention is shown in FIG. 3. This refill 2 comprises a wick 21, through which the volatile substances evaporate. Said refill 2 is placed in a releasable manner in a housing of the casing 1 and is exchanged for another one when the volatile substances therein have run out.

Even though that reference has been made to a specific embodiment of the invention, it is evident for a person skilled in the art that numerous variations and changes may be made to the evaporation device described, and that all the aforementioned details may be substituted by other technically equivalent ones, without detracting from the scope of protection defined by the attached claims.

The invention claimed is:

1. A device for evaporating volatile substances, comprising:
 a casing provided with a housing for placement of a refill containing the volatile substances, said casing comprising a surface; and
 at least one coupling element provided on the surface in order to couple an additional element, said additional element comprising a frame and a releasable sheet,
 wherein said at least one coupling element is a slot placed directly adjacent at least one portion of an outer edge the surface.

2. The device for evaporating volatile substances according to claim 1, wherein said at least one coupling element is a plurality of recesses and/or projections that are complementary to projections and/or recesses of said additional element.

3. The device for evaporating volatile substances according to claim 1, wherein said casing comprises a front body and a rear body able to be coupled together.

4. The device for evaporating volatile substances according to claim 3, wherein said surface is arranged in said front body.

5. The device for evaporating volatile substances according to claim 1, wherein the casing further comprises a ventilation body, through which the volatile substances evaporate.

6. The device for evaporating volatile substances according to claim 1, wherein said casing further comprises a plug for a connection thereof to an electrical grid.

7. The device for evaporating volatile substances according to claim 1, wherein an area of said releasable sheet is larger than an area of the surface of said casing.

8. The device for evaporating volatile substances according to claim 1, wherein the frame and/or the releasable sheet of said additional element is made of plastic.

\* \* \* \* \*